(12) United States Patent
Bartlett et al.

(10) Patent No.: US 7,781,572 B2
(45) Date of Patent: Aug. 24, 2010

(54) NANOSIZED CAROTENOID CYCLODEXTRIN COMPLEXES

(75) Inventors: Mark R. Bartlett, Orem, UT (US); Angela Mastaloudis, Holladay, UT (US); Carsten R. Smidt, Sandy, UT (US); Stephen J. Poole, Springville, UT (US)

(73) Assignee: NSE Products, Inc., Provo, UT (US)

( * ) Notice: Subject to any disclaimer, the term of this patent is extended or adjusted under 35 U.S.C. 154(b) by 549 days.

(21) Appl. No.: 11/538,766

(22) Filed: Oct. 4, 2006

(65) Prior Publication Data

US 2007/0191307 A1 Aug. 16, 2007

Related U.S. Application Data

(60) Provisional application No. 60/724,051, filed on Oct. 5, 2005.

(51) Int. Cl.
| | |
|---|---|
| C07G 3/00 | (2006.01) |
| C07G 11/00 | (2006.01) |
| C07H 15/00 | (2006.01) |
| C07H 17/00 | (2006.01) |
| C07H 1/00 | (2006.01) |
| C07H 3/00 | (2006.01) |
| C08B 37/00 | (2006.01) |
| A01N 43/04 | (2006.01) |
| A61K 31/715 | (2006.01) |

(52) U.S. Cl. ............. 536/4.1; 536/124; 514/58
(58) Field of Classification Search ............ 536/4.1, 536/124; 514/58
See application file for complete search history.

(56) References Cited

U.S. PATENT DOCUMENTS

| | | | |
|---|---|---|---|
| 5,189,149 A | 2/1993 | Bruzzese et al. | |
| 5,221,735 A | 6/1993 | Leuenberger et al. | |
| 5,321,014 A | 6/1994 | Janz et al. | |
| 5,834,445 A | 11/1998 | Sikorski et al. | |
| 6,048,736 A | 4/2000 | Kosak | |
| 6,436,414 B1 | 8/2002 | Raschke et al. | |
| 6,515,018 B1 * | 2/2003 | Fuhrman et al. | 514/458 |
| 6,825,179 B2 | 11/2004 | Nielsen et al. | |
| 6,864,246 B2 | 3/2005 | Bougaret et al. | |
| 6,884,885 B2 | 4/2005 | Qi | |
| 2004/0109920 A1 * | 6/2004 | Reuscher et al. | 426/73 |
| 2005/0184275 A1 | 8/2005 | Mario-Gutierrez et al. | |
| 2007/0212433 A1 * | 9/2007 | Smidt et al. | 424/758 |

FOREIGN PATENT DOCUMENTS

| | | |
|---|---|---|
| WO | WO 96/40262 | 12/1996 |
| WO | WO 03/053475 | 7/2003 |
| WO | WO 2004/005353 | 1/2004 |

OTHER PUBLICATIONS

Aoki, H., Kieu, N.T.M., Kuze, N., Tomisaka, K., Chuyen, N.V. (2002) Carotenoid Pigments in GAC Fruit (*Momordica cochinchinensis* SPRENG). Bioscience, Biotechnology and Biochemistry, vol. 66, No. 11, p. 2479-2482.*
Ansel, H.C., Allen, Jr., L.V., Popovich, N.G. (1999) Pharmaceutical Dosage Forms and Drug Delivery Systems, published by Lippincott Williams & Wilkins, p. 180 and 190-193.*
Kris-Etherton, P.M., Harris, W.S., Appel, L.J. (2002) Fish Consumption, Fish Oil, Omega-3 Fatty Acids, and Cardiovascular Disease. Circulation, vol. 106, No. 21, p. 2747-2757.*
Rosenthal, R. L., Effectiveness of Altering Serum Cholesterol Levels without Drugs. Baylor University Medical Proceedings, 2000, 13:351-355, (Oct. 2000), specifically p. 353, second column last paragraph through p. 354, first column, third full paragraph.

* cited by examiner

*Primary Examiner*—Leigh C Maier
*Assistant Examiner*—Scarlett Goon
(74) *Attorney, Agent, or Firm*—Thorpe North & Western LLP

(57) ABSTRACT

Methods for the preparation of nanosized nutrient formulations for enhanced absorption of nutritional agents. The methods include the complexation of cyclodextrin with carotenoids and incorporation of the complexes into the nutritional supplements without intermediate collection, isolation, and drying steps.

5 Claims, No Drawings

NANOSIZED CAROTENOID
CYCLODEXTRIN COMPLEXES

This application claims the benefit of U.S. Provisional Patent Application Ser. No. 60/724,051 filed on Oct. 5, 2005.

FIELD OF THE INVENTION

The present invention relates to compositions and related processes which increase the bioavailability of carotenoids provided by nutritional supplement formulations containing such nutrients. Accordingly, the present invention involves the fields of chemistry, food science, biology and nutrition.

BACKGROUND OF THE INVENTION

Carotenoids are highly colored fat-soluble plant pigments that are well known for their nutritional and health benefits. Benefits associated with carotenoids include antioxidant activity as well as conversion to vitamin A. Studies indicate that higher dietary intake of carotenoids offers protection against developing certain cancers, macular degeneration, cataracts, heart disease, and other health conditions linked with oxidative or free radical damage. Because of the significant and desirable health benefits associate with carotenoids, nutritional companies have been quick to place carotenoid containing products on the market. Unfortunately, carotenoids are not readily soluble in intestinal fluid and therefore their absorption into the body is often quit low.

Therefore, methods and systems for improving carotenoid absorption and bioavailability, as well as that of other nutrients, continues to be sought.

SUMMARY

Accordingly, the present invention provides methods and compositions for improving the bioavailability of nutrients, particularly, carotenoids, primarily through specific manufacturing techniques.

In one embodiment the invention includes a method for manufacturing a carotenoid containing nutritional supplement. The method includes mixing an amount of cyclodextrin with water to form a water/cyclodextrin slurry at 50° C., admixing an amount of at least one carotenoid to the water/cyclodextrin slurry to form a preblend composition including cyclodextrin carotenoid complexes, pulling a vacuum over the preblend composition and thoroughly mixing the preblend composition for a minimum of 1 hour, forming a final blend by mixing under a vacuum the undried preblend composition with additional nutritional components at a temperature of about 40-45° C. milling the final blend in a vacuum, encapsulating the milled final blend.

In one aspect of the invention the cyclodextrin is a gamma-cyclodextrin. In another aspect of the invention the at least one carotenoid is selected from a group consisting of astaxanthin, lycopene, zeaxanthin, beta-carotene, and combinations thereof. In a further aspect of the invention additional nutritional components can be incorporated into the composition including fish oil, beeswax, vitamin A, vitamin E, lutein, limonene, krill oil, and combinations thereof.

In another embodiment of the invention a method for manufacturing a carotenoid containing nutritional supplement includes heating an amount of water to 50° C. in a blending apparatus, mixing an amount of cyclodextrin with water to form a water/cyclodextrin slurry, admixing an amount of at least one carotenoid to the water/cyclodextrin slurry to form a preblend composition including cyclodextrin carotenoid complexes, pulling a vacuum over the preblend composition and thoroughly mixing the preblend composition for a minimum of 1 hour in a separate mixing container, forming a fish oil blend by mixing an amount of fish oil at a temperature of 60° C. until thoroughly mixed and then allowing to cool to 40-45° C., forming a final blend by mixing under a vacuum the undried preblend composition with the fish oil/beeswax blend a temperature of about 40-45° C. optionally admixing additional nutritional components to the final blend, cooling final blend mixture to 25-28° C., milling the final blend in a vacuum to reduce particle size, encapsulating the milled final blend.

DETAILED DESCRIPTION

Definitions

In describing and claiming the present invention, the following terminology will be used in accordance with the definitions set forth below.

The singular forms "a," "an," and, "the" include plural referents unless the context clearly dictates otherwise. Thus, for example, reference to a nutritional supplement containing "a cyclodextrin component" includes one or more cyclodextrin components and reference to "the carotenoid" includes reference to one or more carotenoids.

As used herein, "subject" refers to a mammal that may benefit from the administration of a nutritional supplement or method of this invention. Examples of subjects include humans, and may also include other animals such as horses, pigs, cattle, dogs, cats, rabbits, and aquatic mammals.

As used herein, the terms "formulation" and "composition" are used interchangeably and refer to a mixture of two or more compounds, elements, or molecules.

As used herein, "single dose" refers to one or multiple capsule delivery units capable of delivering the desired amount of carotenoid to a subject.

As used herein, an "effective amount," and "sufficient amount" may be used interchangeably and refer to an amount of an ingredient which, when included in a chew composition, is sufficient to achieve an intended compositional or physiological effect. For example, a "sufficient amount" of carotenoid extract would be the minimum amount needed to have a nutritional affect. Further, a "therapeutically effective amount" refers to an amount of a carotenoid which is sufficient to achieve a desired physiological effect. The determination of an effective amount is well within the ordinary skill in the art of pharmaceutical, neutraceutical, herbaceutical, cosmetic, and medical sciences. See, for example, Meiner and Tonascia, "Clinical Trials: Design, Conduct, and Analysis," *Monographs in Epidemiology and Biostatistics*, Vol. 8 (1986), incorporated by reference in its entirety.

The term "admixed" means that the drug and/or enhancer can be dissolved, dispersed, or suspended in the carrier. In some cases, the drug may be uniformly admixed in the carrier.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

Invention

The present invention encompasses a process for preparing a carotenoid containing nutritional supplement including the formation of a carotenoid-cyclodextrin complex. Carotenoids are well known in the nutritional arts for providing a variety of health benefits. The present invention provides for methods of manufacturing a readily absorbable carotenoid containing nutritional supplement that is easy to perform, is time and cost effective, and results in a product in which the carotenoid is both highly stable and readily bioavailable.

It is well known in the nutritional supplement arts that carotenoids have poor solubility in intestinal fluids. This poor solubility leads to poor absorption or uptake of the carotenoids into systemic circulation. Another factor contributing to poor absorption of carotenoids is that carotenoids tend to aggregate into large particles which are not readily digested or absorbed. Cyclodextrins can encapsulate the poorly soluble compounds increasing their solubility and inhibiting the aggregation which typically occurs. The smaller encapsulated compounds are often referred to as nano-particles because of their extremely small size.

The present invention provides a streamlined method for the manufacture of nutritional supplements containing carotenoid-cyclodextrin complexes. In particular the method provides for the production and subsequent direct incorporation of carotenoid-cyclodextrin complexes into a nutritional supplement without the intermediary steps of collection, isolation, and drying. Because the carotenoid-cyclodextrin complexes can be directly incorporated into nutritional supplements without intermediary steps, costs are reduced.

The method of the present invention includes creating a cyclodextrin slurry by combining an amount of cyclodextrin with water. The preferred temperature for the manufacture of the slurry is from to 50° C. All types of cyclodextrins and combinations thereof may be used in the present invention including α-cyclodextrin, γ-cyclodextrin, and β-cyclodextrin. In one embodiment the cyclodextrin used is γ-cyclodextrin. In another embodiment the cyclodextrin is a mixture of γ-cyclodextrin, and β-cyclodextrin. The cyclodextrin and water mixture should be mixed for a period of about 20 minutes or until a caramel color is observed. The role of the water is to hydrate the cyclodextrin. Hydrated cyclodextrin can than better complex with the carotenoids. Once the cyclodextrin slurry is formed carotenoids can be admixed therein. The mixing of the carotenoid/cyclodextrin mixture should continue for a minimum of 1 hour at a temperature of from about 40° C. to about 50° C. Mixing the carotenoid/cyclodextrin mixture at high shear can enhance or increase the rate of reaction and thereby the rate of formation of the carotenoid-cyclodextrin complex. However, such lower shear values generated by lower mixing speeds can also be used effectively to form the carotenoid-cyclodextrin complexes.

The carotenoids which can be used in the present invention include any carotenoid known in the art to have positive health benefits. The preferred carotenoids for use in the present invention are astazanthin, lycopene, zeaxanthin, beta-carotenes, lutein, and mixtures thereof. When possible, it is preferred that a vacuum should be pulled over the carotenoid containing compositions of the present invention so as to slow or inhibit the degradation of the carotenoids. Another acceptable method of maintaining the stability of the carotenoid is to keep the carotenoids containing mixtures under nitrogen.

As the carotenoid/cyclodextrin composition is mixed, carotenoid-cyclodextrin complexes begin to precipitate out of solution making the solution more viscous. This increase in viscosity can be used as an indicator of successful formation of the carotenoid-cyclodextrin complex. In traditional carotenoid-cyclodextrin complex manufacturing methods the precipitated complexes are collected, isolated and dried at this point in the process. By so doing the water originally present in the cyclodextrin slurry is eliminated. In the method of the present invention the complexes are maintained in the preblend slurry, including the water. The ability of the manufacturing process of the present invention to eliminate the drying process reduces both the time and cost associated with the process.

After formation of the carotenoid-cyclodextrin complexes, the preblend slurry can then be admixed with additional nutritional components at a temperature of 40° C. to 45° C. to form a final blend. The final blend is mixed thoroughly for a minimum of 20 minutes. Examples of additional nutritional components which can be used in the present invention include but are not limited to vitamin A, vitamin E, lutein, fish oil, limonene, beeswax, and combinations thereof. It is preferred that the final blend be mixed with fish oil. Any type of fish oil known to one skilled in the art can be used with the present invention. For the purposes of the present invention krill oil is included as a fish oil.

In addition to the health benefits which are inherent in fish oil, the addition of the fish oil to the preblend slurry helps to stabilize and solubilize any uncomplexed carotenoids found in the preblend slurry and further enhances the bioavailability of both the complexed and uncomplexed carotenoids. It has been determined that when the carotenoid-cyclodextrin complexes of the present invention are co-administered with a minimum amount of fish oil the bioavailability of the carotenoids is increased above that of the carotenoid-cyclodextrin complex alone. Without being limited by theory, it is believed that this increase in bioavailability is due, at least in part, to fish oils stimulation of lipase enzymes in the gut which in turn facilitate the absorption of the carotenoids. In a preferred embodiment the fish oil comprises from about 70 wt % to about 90 wt % of the final blend composition. In another embodiment the fish oil can comprise from about 75 wt % to about 85 wt % of the final blend composition. When other nutritional components, particularly readily oxidizable components such as Vitamin A and vitamin E, are included in the final blend composition the fish oil also acts to stabilize and protect those components.

Once the final blend composition is complete, it is milled to assure small particle size of the complexed carotenoids. After milling the final blend can be directly encapsulated or stored in an air tight container under nitrogen. In a preferred embodiment of the present invention, the final blend is encapsulated into soft gelatin capsules. The compositions produced by the methods of the present invention are intended to be delivered to subjects so as to provide therapeutically effective amounts of carotenoids to the subject. Such amounts are readily determinable by one of ordinary skill in the art based on the concentrations of the carotenoids in the invention compositions.

In addition to the method, the present invention provides a composition and related method for providing enhanced bioavailability of carotenoids. Specifically, it has been found that when fish oil is included in the final blend composition as described above, the bioavailability of the carotenoids is unexpectedly increased above the bioavailability of the carotenoid/cyclodextrin complex alone and a fish oil/carotenoid mixture alone. As discussed above, it is believed that the unexpected increase of bioavailability is due, at least in part, to fish oils stimulation of lipase enzymes in the gut which in turn facilitate the absorption of the carotenoids.

The example provided below is illustrative of only one embodiment of making a carotenoid containing nutritional supplement of the present invention. While the processing conditions and ingredients may be preferred, no limitation thereto is to be inferred.

Example 1

A stable carotenoid containing nutritional supplement is preparing according to the following steps.

1. 5.640 kg of water is added to a blender and heated to 50° C. Temperature is confirmed before adding cyclodextrin.

2. Blades of blender are removed from blender container and 4.070 kg of gamma-cyclodextrin (Cavamax V Wacker Biochem) is added and initially hand mixed, and then mechanically mixed for at least 30 minutes or until a cyclodextrin water slurry is formed. The slurry is caramel in color.

3. The following carotenoids are added in the amounts shown in the following table:

| Carotenoid | Activity (% or IU/mg) | kg |
| --- | --- | --- |
| Beta-Carotene (30% Fluid Suspension, B. trispora) | 500.00 IU | 0.273 |
| Beta-Carotene (Caromin 13% b 6.5% a; oil; palm fruit) | 13.000% | 0.689 |
| Astaxanthin, 5% OIL BioAstin (H. pluvialis) | 5.000% | 0.224 |
| Lycopene (20% Oil Susp.) LycoVit synthetic | 20.000% | 0.560 |
| Zeaxanthin (20% Fluid Susp.) | 20.000% | 0.056 |

4. A vacuum is pulled over the mixing container and the composition is mixed on a low speed (9.6 rpm) for at least 1 hour at a temperature of 4-45° C. and carotenoid cyclodextrin complexes form. (Note: as the carotenoids react with the cyclodextrins the compound will precipitate and the mixture increases in viscosity which is an indication of a successful complexation reaction.)

5. After at least one hour of mixing the mixer container containing the carotenoid-cyclodextrin complex are immediately removed and added to a main mixer containing a fish oil beeswax blend. The fish oil and beeswax blend is made by adding approximately 6.1 kg of beeswax and 73.2 kg of fish oil to the mixer and blending at 60° C. to until thoroughly mixed. The composition is then cooled to 40-45° C. before the carotenoid-cyclodextrin complex is added. A small amount of the fish oil/beeswax composition is used to rinse the carotenoid-cyclodextrin complex into the mixer container.

6. Additional components can then be added to the mixer. The components and the amounts added are shown in the table below:

| Ingredient | Activity (% or IU/mg) | kg |
| --- | --- | --- |
| Vitamin A (Palmitate, liquid 1,700 USP) | 1600.0 IU | 0.043 |
| Vitamin E (d-alpha-tocopherol 1490 oil) | 1.430 IU | 2.988 |
| Vitamin E, 60% g-t, 6.8% a-t, 20% d-t, 1.4% b-t, MTS-90G Oil | 60.000% | 2.671 |
| Vitamin E Tocotrienols (50% E&TT, Fr. Palm Oil) | 38.000% | 0.028 |
| Lutein (Ester, Xangold, oil susp, 15%) | 15.000% | 0.298 |
| Krill Oil | 100.000% | 2.035 |
| D-Limonene (liquid) | 95.000% | 1.071 |

7. After the addition of the carotenoid/cyclodextrin complex and the other ingredients the mixture a vacuum is pulled over the mixer container and the mixture is mixed using high shear for 20 minutes at 20-45° C. The mixture is then allowed to cool to 25-28° C. and is removed from the mixer and milled to reduce the particle size.

8. After milling the mixture can be stored in a sealed container under nitrogen or encapsulated immediately. Encapsulation is done in a soft gelatin capsule. Each soft gelatin capsule contains about 1.2 grams of the milled final composition.

Example 2

A study was performed to determine the effect of the composition of claim 1 on the Skin Carotenoid Scores (SCS) of subjects. The study involved the use of Raman Spectroscopy to assess changes in Skin Carotenoid Scores over an eighteen week period of supplementation with the Composition of example 1 in comparison to a placebo.

Fifty two subjects between 18 and 65 years of age qualified for the study participation. Food frequency and health history questionnaires were used to screen inclusion criteria, and the Pharmanex BioPhotonic Scanner was used to assess skin carotenoid levels. Individuals taking antioxidant supplements, having high exposure to sunlight or tanning bed use, pregnant women, or individuals using sunless tanning products were excluded from the study. All subjects were healthy non-smokers consuming typical U.S. diets containing less than five daily servings of fruit and vegetables, and had baseline Raman Intensity Scores between 13,000 and 35,000 Raman Intensity Counts. Participants were instructed to maintain their dietary and exercise habits throughout the duration of the study. Subjects (n=52) meeting study criteria were randomly assigned in a double blind manner to one of two groups, composition of example 1 (n=27) or placebo (n=25).

Subjects were given their respective capsules, placebo or composition of Example 1, and were instructed to take them twice daily (once with their morning meal and once with their evening meal). The dosage amount for the Example 1 participants included two softgel capsules twice daily. The placebo taken twice daily included also included two softgel capsules which contained omega-3 fatty acids but no carotenoids.

The results of the study showed an unexpectedly high increase of the Skin Carotenoid Scores. Specifically, the average increase for those taking the composition of Example 1 was 17,757 Raman Intensity counts after the eighteen weeks compared to approximately no change for the placebo participants. Throughout the 18 week study the Carotenoid Scanner Score continually increased with no apparent plateau effect.

While the forgoing example is illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

We claim:

1. A method for manufacturing a carotenoid containing nutritional supplement comprising:
   a) heating an amount of water to 50° C. in a blending apparatus;
   b) mixing an amount of cyclodextrin with water to form a water/cyclodextrin slurry;
   c) admixing an amount of at least one carotenoid to the water/cyclodextrin slurry to form a preblend composition including cyclodextrin carotenoid complexes;
   d) pulling a vacuum over the preblend composition and thoroughly mixing the preblend composition for a minimum of 1 hour;
   e) in a separate mixing container, warming an amount of fish oil to a temperature to 40° C. to 45° C.;
   f) forming an undried final blend by mixing under a vacuum the undried preblend composition with the fish oil at a temperature of about 40° C. to 45° C.;
   g) optionally admixing additional nutritional components to the undried final blend;
   h) cooling the undried final blend mixture to 25° C. to 28° C.;
   i) milling the undried final blend in a vacuum to reduce particle size; and
   j) encapsulating the milled undried final blend.

2. The method of claim 1, wherein the cyclodextrin is γ-cyclodextrin.

3. The method of claim 1, wherein the cyclodextrin is a combination of γ-cyclodextrin and β-cyclodextrin.

4. The method of claim 1, wherein the at least one carotenoid is selected from a group consisting of astaxanthin, lycopene, zeaxanthin, beta-carotene, lutein and mixtures thereof.

5. The method of claim 1, wherein the additional nutritional components are selected from the group consisting of beeswax, vitamin A, vitamin E, D-limonene, and mixtures thereof.

* * * * *